(12) United States Patent
Woo et al.

(10) Patent No.: US 10,515,280 B2
(45) Date of Patent: Dec. 24, 2019

(54) APPARATUS, VEHICLE INCLUDING THE SAME, AND CONTROL METHOD FOR THE SAME

(71) Applicants: HYUNDAI MOTOR COMPANY, Seoul (KR); KIA MOTORS CORPORATION, Seoul (KR)

(72) Inventors: Seunghyun Woo, Seoul (KR); Gi Beom Hong, Seoul (KR); Daeyun An, Seoul (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 0 days.

(21) Appl. No.: 16/207,772

(22) Filed: Dec. 3, 2018

(65) Prior Publication Data

US 2019/0325240 A1    Oct. 24, 2019

(30) Foreign Application Priority Data

Apr. 24, 2018  (KR) .......................... 10-2018-0047063

(51) Int. Cl.
| | | |
|---|---|---|
| G08B 23/00 | (2006.01) | |
| G06K 9/00 | (2006.01) | |
| A61B 5/18 | (2006.01) | |
| A61B 5/16 | (2006.01) | |
| B60W 40/08 | (2012.01) | |
| G06K 9/62 | (2006.01) | |

(52) U.S. Cl.
CPC .......... *G06K 9/00845* (2013.01); *A61B 5/165* (2013.01); *A61B 5/18* (2013.01); *B60W 40/08* (2013.01); *G06K 9/00315* (2013.01); *G06K 9/00355* (2013.01); *G06K 9/6257* (2013.01); *B60W 2040/089* (2013.01); *B60W 2040/0872* (2013.01)

(58) Field of Classification Search
CPC ........... G06K 9/00845; G06K 9/00302; G06K 9/00255; G06K 9/00288; G06K 9/00281; A61B 5/0205; A61B 5/165
See application file for complete search history.

(56) References Cited

U.S. PATENT DOCUMENTS

| | | | |
|---|---|---|---|
| 9,934,667 B1* | 4/2018 | Fields | ..................... G08B 21/02 |
| 2012/0330173 A1* | 12/2012 | Park | ..................... A61B 5/6893 |
| | | | 600/521 |

FOREIGN PATENT DOCUMENTS

| | | |
|---|---|---|
| JP | 2011123734 A | 6/2011 |
| JP | 2017010206 A | 1/2017 |
| JP | 2017033470 A | 2/2017 |
| KR | 10-2014-0034996 A | 3/2014 |
| KR | 10-2016-0118633 A | 10/2016 |

(Continued)

*Primary Examiner* — Toan N Pham
(74) *Attorney, Agent, or Firm* — Morgan, Lewis & Bockius LLP

(57) ABSTRACT

An apparatus includes: a storage configured to store a data structure including first one or more feature points hierarchically listed and a contribution list including information about a contribution rank of each of second one or more feature points; and a controller configured to compare the first one or more feature points in the data structure with the second one or more feature points of the contribution list, and to determine whether to update the data structure based on a comparison result.

20 Claims, 8 Drawing Sheets

(56) References Cited

FOREIGN PATENT DOCUMENTS

KR  10-2017-0002100 A  1/2017
KR  10-2017-0028631 A  3/2017

* cited by examiner

FIG. 5

| FEATURE POINT | CONTRIBUTION RANK | IMPORTANCE |
|---|---|---|
| A1(13 Interocular Distance MEAN) | 1 | 0.3092 |
| B1(102 EEG_Meditation MEAN) | 2 | 0.2944 |
| D1(9 Valence MEAN ) | 3 | 0.2915 |
| A2(104 Cal GSR (Shimmer Sensor) MEAN) | 4 | 0.2904 |
| B2(71 AU4 Evidence MEAN) | 5 | 0.277 |
| A3(99 Roll Degrees MEAN) | 6 | 0.2666 |
| E1(68 AU1 Evidence MEAN) | 7 | 0.2647 |
| C2(10 Valence STDEV) | 8 | 0.2596 |
| ⋮ | ⋮ | ⋮ |

APPARATUS, VEHICLE INCLUDING THE SAME, AND CONTROL METHOD FOR THE SAME

CROSS-REFERENCE TO RELATED APPLICATION

This application is based on and claims priority under 35 U.S.C. § 119 to Korean Patent Application No. 10-2018-0047063, filed on Apr. 24, 2018 in the Korean Intellectual Property Office, the disclosure of which is incorporated by reference in its entirety.

TECHNICAL FIELD

The present disclosure relates to an apparatus, a vehicle including the same, and a control method of the vehicle.

BACKGROUND

In modern society, vehicles are one of the most common means of transportation, and the number of people using the vehicles has been continuously increasing. The development of vehicle technologies is changing our lives a lot, such as making it easy for us to take a long-distance trip and making lives become easier.

In recent years, technologies have been developed to determine a driver's emotion and increase the driver's convenience in accordance with the driver's emotion. Among them, there is a technology using biometrics to determine the driver's emotion.

The biometrics enables recognizing a body part of the person to perform emotion determination, such as voice recognition, face recognition, hand gesture recognition, or heartbeat recognition. Since the biometrics uses a body part unique to the person, which is changed by the person's emotion, it makes a highly accurate determination on the emotion, and thus, many studies are being conducted on the biometrics.

SUMMARY

An aspect of the present disclosure is to provide an apparatus, a vehicle including the same, and a control method of the vehicle, by which a data structure used to determine a driver's emotion is evaluated to make an accurate determination on the driver's emotion.

Additional aspects of the disclosure will be set forth in part in the description which follows and, in part, will be obvious from the description, or may be learned by practice of the disclosure.

In accordance with an exemplary embodiment of the present disclosure, an apparatus includes: a storage configured to store a data structure including first one or more feature points hierarchically listed and a contribution list including information about a contribution rank of each of second one or more feature points; and a controller configured to compare the first one or more feature points with the second one or more feature points. The controller may determine whether to update the data structure based on a comparison result.

The controller may replace a feature point of the level with a feature point of the contribution list when the feature point of the level and the feature point of the contribution list match.

The controller may compare a feature point included in another hierarchy level with the feature point of the contribution list when the feature point included in the level and the feature point of the contribution list do not match.

The controller may compare the feature point included in the level with the feature point of the contribution list having a rank corresponding to the level.

The controller may compare the feature point included in a next higher level with the feature point of the contribution list having a next higher rank when the feature point included in the level and the feature point of the contribution list having the rank corresponding to the level do not match.

The controller may replace the feature point of the level with the feature point of the contribution list when the feature point included in the level and the feature point of the contribution list match, and evaluate accuracy of the data structure in which the feature point is replaced.

The controller may determine whether to update the data structure based on a result of the accuracy evaluation.

The controller may store the data structure in which the feature point is replaced in the storage when the accuracy is equal to or greater than a preset expected value.

In accordance with another exemplary embodiment of the present disclosure, a vehicle includes: a biometric sensor configured to collect biometric information of a driver; an apparatus having a controller and a storage and configured to store a data structure including first one or more feature points hierarchically listed and a contribution list including information about a contribution rank of each of the second one or more feature points, compare the first one or more feature points with the second one or more feature points, and determine whether to update the data structure based on a comparison result; and a main controller, which communicates with the apparatus and the biometric sensor, configured to determine the driver's emotion using the data structure and the biometric information.

The apparatus may replace a feature point of the level with a feature point of the contribution list when the feature point of the level and the feature point of the contribution list match.

The apparatus may compare a feature point included in another hierarchical level with the feature point of the contribution list when the feature point included in the level and the feature point of the contribution list do not match.

The apparatus may compare the feature point included in the level with the feature point of the contribution list having a rank corresponding to the level.

The apparatus may compare the feature point included in a next higher level with the feature point of the contribution list having a next higher rank when the feature point included in the level and the feature point of the contribution list having the rank corresponding to the level do not match.

The apparatus may replace the feature point of the level with the feature point of the contribution list when the feature points included in the level and the feature point of the contribution list match, and evaluate accuracy of the data structure in which the feature point is replaced.

The apparatus may determine whether to update the data structure based on a result of the accuracy evaluation.

The apparatus may store the data structure in which the feature point is replaced in the storage when the accuracy is equal to or greater than a preset expected value.

The biometric sensor may include a camera configured to recognize the driver's face or a hand gesture.

The biometric sensor may include a microphone configured to recognize the driver's voice.

The vehicle may further include a display configured to display the determination result of the emotion.

In accordance with another exemplary embodiment of the present disclosure, a control method of a vehicle, wherein the vehicle includes a storage for storing a data structure including first one or more feature points hierarchically listed and a contribution list including information about a contribution rank of each of second one or more feature points, the method includes: comparing, by a controller, the first one or more feature points with the second one or more feature points; determining whether to update the data structure based on a comparison result; and determining the driver's emotion using the data structure and biometric information of a driver.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 5 is an exemplary diagram of a contribution list stored in an apparatus;

DETAILED DESCRIPTION

Figure 1:
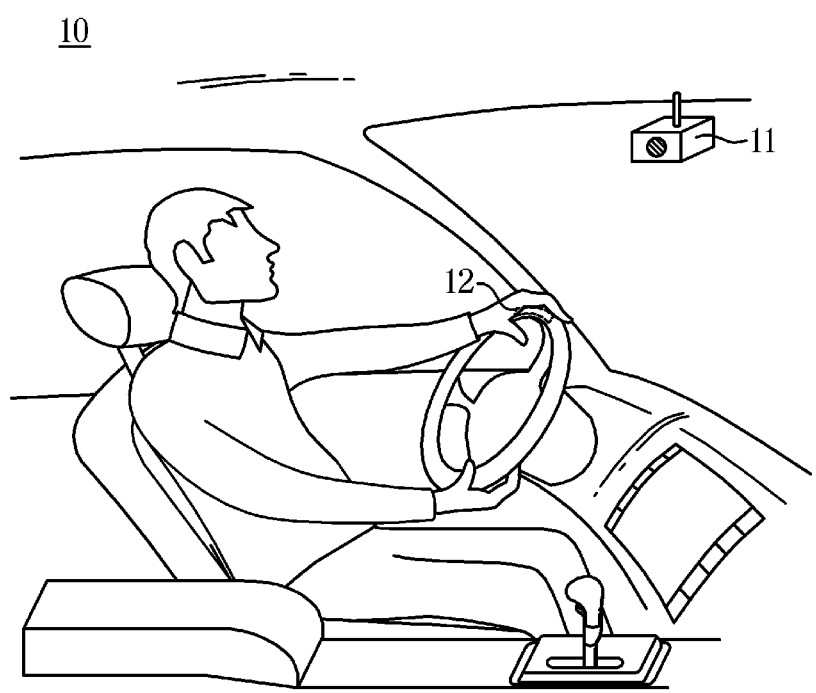
FIG. 1 is a view illustrating the interior of a vehicle according to an exemplary embodiment.

Like reference numerals refer to like elements throughout the specification. Not all elements of embodiments of the present disclosure will be described, and description of what are commonly known in the art or what overlap each other in the embodiments will be omitted. The terms as used throughout the specification, such as "~part," "~module," "~member," "~block," etc., may be implemented in software and/or hardware, and a plurality of "~parts," "~modules," "~members," or "~blocks" may be implemented in a single element, or a single "~part," "~module," "~member," or "~block" may include a plurality of elements.

It will be further understood that the term "connect" or its derivatives refer both to direct and indirect connection, and the indirect connection includes a connection over a wireless communication network.

The term "include (or including)" or "comprise (or comprising)" is inclusive or open-ended and does not exclude additional, unrecited elements or method steps, unless otherwise mentioned.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

It is to be understood that the singular forms "a," "an," and "the" include plural references unless the context clearly dictates otherwise.

Reference numerals used for method steps are merely used for convenience of explanation, but not to limit an order of the steps. Thus, unless the context clearly dictates otherwise, the written order may be practiced otherwise.

Hereinafter, an operation principle and embodiments of the present disclosure will be described with reference to accompanying drawings.

FIG. 1 is a view illustrating the interior of a vehicle according to an exemplary embodiment.

Referring to FIG. 1, a vehicle 10 may be provided with various biometric apparatuses to determine emotions of a driver on board. The biometric apparatuses may include a camera 11 for recognizing the face or a hand motion of the driver, an electrode 12 for measuring a heartbeat, a microphone (not shown) for performing voice recognition, and the like, without being limited thereto.

Figure 2:
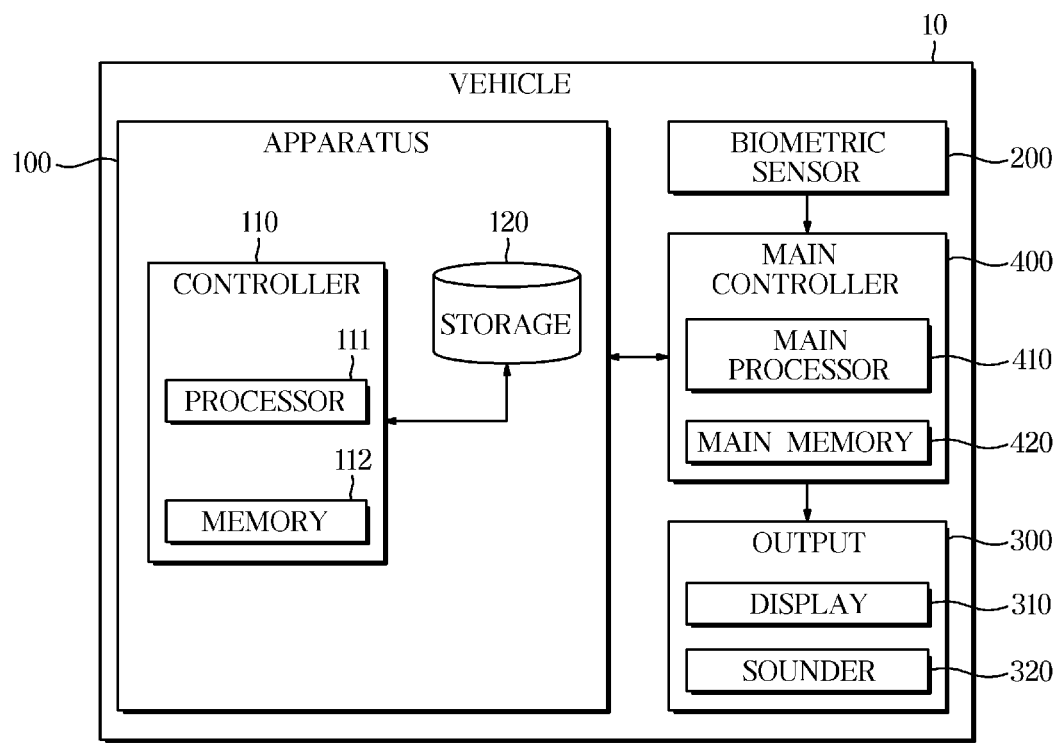
FIG. 2 is a block diagram illustrating a vehicle according to an exemplary embodiment.

Biometric information obtained by the biometric apparatuses may be provided to a main controller 400 in FIG. 2 of the vehicle 10, and the main controller 400 may be used to determine emotions based on a pre-stored data structure.

FIG. 2 is a block diagram illustrating a vehicle according to an exemplary embodiment.

The vehicle 10 may include an apparatus 100 to evaluate a pre-stored data structure and may further include a biometric sensor 200, an output 300, and a main controller 400.

The apparatus 100 may evaluate accuracy of the pre-stored data structure and provide the evaluation result to the main controller 400. To this end, the apparatus 100 may include a controller 110 for controlling operation of components in the apparatus 100 to evaluate the accuracy of the data structure, and a storage 120 for storing the data structure.

The controller 110 may be implemented with a memory 112 that stores an algorithm for controlling the operation of the components in the apparatus 100 or data for a program that reproduces the algorithm and a processor 111 that performs the above-described operation using the data stored in the memory 112. The memory 112 and the processor 111 may be implemented in separate chips.

Alternatively, the memory 112 and the processor 111 may be implemented in a single chip.

The controller 110 may evaluate the accuracy of the data structure stored in the storage 120.

The controller 110 may be an electronic control unit (ECU).

The data structure may include a plurality of feature points and emotion values for biometric information having a hierarchical structure, and may have, for example, a tree structure. The data structure stored in the storage 120 will be described later with reference to FIG. 3.

The controller 110 may determine the appropriateness of the feature points at respective levels in the pre-stored data structure.

Particularly, the controller 110 may evaluate the plurality of feature points separately from the data structure according to a preset reference, assign a rank to each feature point, and generate a contribution list in which the feature points are ranked. Then, the controller 110 may compare a feature point of a level in the data structure with a feature point having a certain rank on the contribution list, and replace the feature point of the level in the data structure with the feature point on the contribution list when the feature points do not match.

The controller 110 may then evaluate the accuracy of the data structure with the feature point replaced and compare the previous accuracy of the data structure stored in the storage 120 with the current accuracy of the data structure evaluated by the controller 110, and store the data structure having higher accuracy in the storage 120. The stored data structure may be used when the main controller 400 performs emotion determination based on the driver's biometric information.

On the other hand, if a feature point of a level in the data structure with a feature point having a certain rank on the contribution list are compared by the controller 110 and matched, the controller 110 may search the next lower level in the data structure and the next lower rank of the contribution list, and compare the feature point of the next lower layer in the data structure with the feature point having the next lower rank on the contribution list. Similarly, the controller 110 may replace the feature point of the next lower layer with the feature point of the next lower rank on the contribution list, when the feature points do not match with each other, and replace the data structure stored in the storage 120 according to the accuracy evaluation result of the data structure in which the feature point is replaced.

A more detailed control process of the controller 110 will be described later.

The storage 120 may store the data structure.

The initial data structure may be stored in the storage 120 in the design process or in a repair process. The data structure thereafter may be stored by the controller 110.

The data structure stored in the storage 120 may be utilized by the main controller 400. The main controller 400 may determine the driver's emotion using the data structure stored in the storage 120.

The storage 120 may be implemented with at least one of a non-volatile memory device, such as cache, read only memory (ROM), programmable ROM (PROM), erasable programmable ROM (EPROM), electrically erasable programmable ROM (EEPROM), a volatile memory device, such as random access memory (RAM), or a storage medium, such as hard disk drive (HDD) or compact disk (CD) ROM, without being limited thereto. The storage 120 may be a memory implemented with a chip separate from a processor, which will be described later, in relation to the controller 110, or may be implemented integrally with the processor in a single chip.

Although the above embodiment has been described in which the storage 120 and the memory 112 of the controller 110 may be implemented as separate chips, it is also possible that the storage 120 and the memory 112 are implemented as a single chip.

The biometric sensor 200 is an apparatus for acquiring biometric information of the driver, and may be the biometric apparatus described with reference to FIG. 1, that is, the camera 11, the electrode 12, and the microphone. The biometric information may be included in the vehicle 10, may directly transmit various biometric information values to the main controller 400, and may transmit the biometric information to the main controller 400 through the wired/wireless communication network provided outside the vehicle 10. The biometric sensor 200 may be connected to or embedded in the main controller 400.

The output 300 may output the evaluation result of the apparatus 100 or the emotion determination result of the main controller 400 to the driver. The output 300 may include at least one of a display 310 for displaying content and a sounder 320 for delivering audio content.

For example, the display 310 may display the data structure stored in the storage 120, display the accuracy of the data structure evaluated by the apparatus 100 in a numerical value, or display the driver's emotion determined by the main controller 400 in the form of letters, emoticons, pictures, or the like.

The display may be provided as a cathode ray tube (CRT), a digital light processing (DLP) panel, a plasma display panel (PDP), a liquid crystal display (LCD) panel, an electro luminescence (EL) panel, an electrophoretic display (EPD) panel, an electrochromic display (ECD) panel, a light emitting diode (LED) panel or an organic light emitting diode (OLED) Panel, but the present disclosure is not limited thereto.

The sounder 320 may output the accuracy of the data structure evaluated by the apparatus 100 in the form of a voice, or output the driver's emotion determined by the main controller 400 in the form of the voice or music.

The sounder 320 may be a speaker, an amplifier, or the like that outputs sound, but is not limited thereto.

The main controller 400 may extract feature points of the biometric information provided from the biometric sensor 200 of the vehicle 10 and derive an emotion value of the driver corresponding to the resultant values of the extracted feature points. The feature point of the biometric information may be a feature point of the data structure stored in the apparatus 100, and the emotion value may be an emotion value of the data structure stored in the apparatus 100.

The main controller 400 may derive the emotion value of the driver corresponding to the driver's biometric information based on the data structure stored in the storage 120 of the apparatus 100.

The main controller 400 may be implemented with a main memory 420 that stores an algorithm for controlling the operation of components in the vehicle 10 or data for a program that reproduces the algorithm and a main processor 410 that performs the above-described operation using the data stored in the main memory 420. The main memory 420 and the main processor 410 may be implemented in separate chips. Alternatively, the main memory 420 and the main processor 410 may be implemented in a single chip.

The main controller 400 may be implemented as an electronic control unit (ECU) that controls operation of a power generating device, a power transmitting device, a driving device, a steering device, a braking device, a suspension device, a transmission, a fuel device, various safety devices, and various sensors of the vehicle 10.

The main controller 400 and the controller 110 of the apparatus 200 may be implemented as separate hardware components or as a single hardware component to implement software components for respective functions.

Hereinafter, a method of the vehicle 10 including the apparatus 100 evaluating a data structure and determining the driver's emotion using the evaluated data structure according to an embodiment of the present disclosure will be described with reference to FIGS. 3 to 7.

Figure 3:
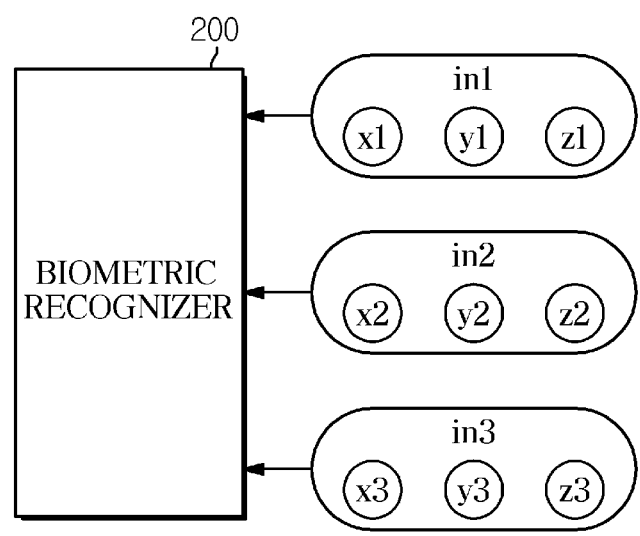
FIG. 3 is a conceptual diagram illustrating grouping of biometric information values input to a main controller.

FIG. 3 is a conceptual diagram illustrating grouping of biometric information values input to a main controller.

Referring to FIG. 3, when the main controller 400 acquires a plurality of biometric information values (x, y, z) one or more times through the biometric sensor 200, if a group of a plurality of biometric information values obtained each time is referred to as a biometric information group (in), the plurality of biometric information values (x, y, z) included in each biometric information group (in) may be collected by the same or different biometric sensor(s) 200.

Since the biometric information may appear differently depending on a measurement point of time or a person, even if each of groups (in1, in2, and in3) has biometric information values (x1, y1, z1; x2, y2, z2; x3, y3, z3) obtained using one or more identical biometric devices, the biometric information values (x1, x2, and x3; y1, y2, and y3; z1, z2, and z3) of the groups (in1, in2, and in3) obtained using the same biometric apparatus may be different from each other.

For example, in a case where a camera and a microphone are provided as the biometric sensor 200 and the face image of a driver by the camera, the voice tone by the microphone, and the pupil image by the camera are acquired as the biometric information, the main controller 400 may receive facial image data (x1), voice data (y1), and pupil image data (z1) for the first group (in1), facial image data (x2), voice data (y2), and pupil image data (z2) for the first group (in2), and facial image data (x3), voice data (y3), and pupil image data (z3) for the first group (in3).

Since facial image data, voice data, and pupil image data differ according to time or driver, the facial image data (x1, x2, and x3) may be different from each other, the voice data (y1, y2, and y3) may be different from each other, and the pupil image data (z1, z2, and z3) may be different from each other.

The main controller 400 extracts a feature point of the driver's biometric information obtained based on a data structure stored in the storage 120 of the vehicle 100 and derives an emotion result value of the driver corresponding to the feature value.

Figure 4:
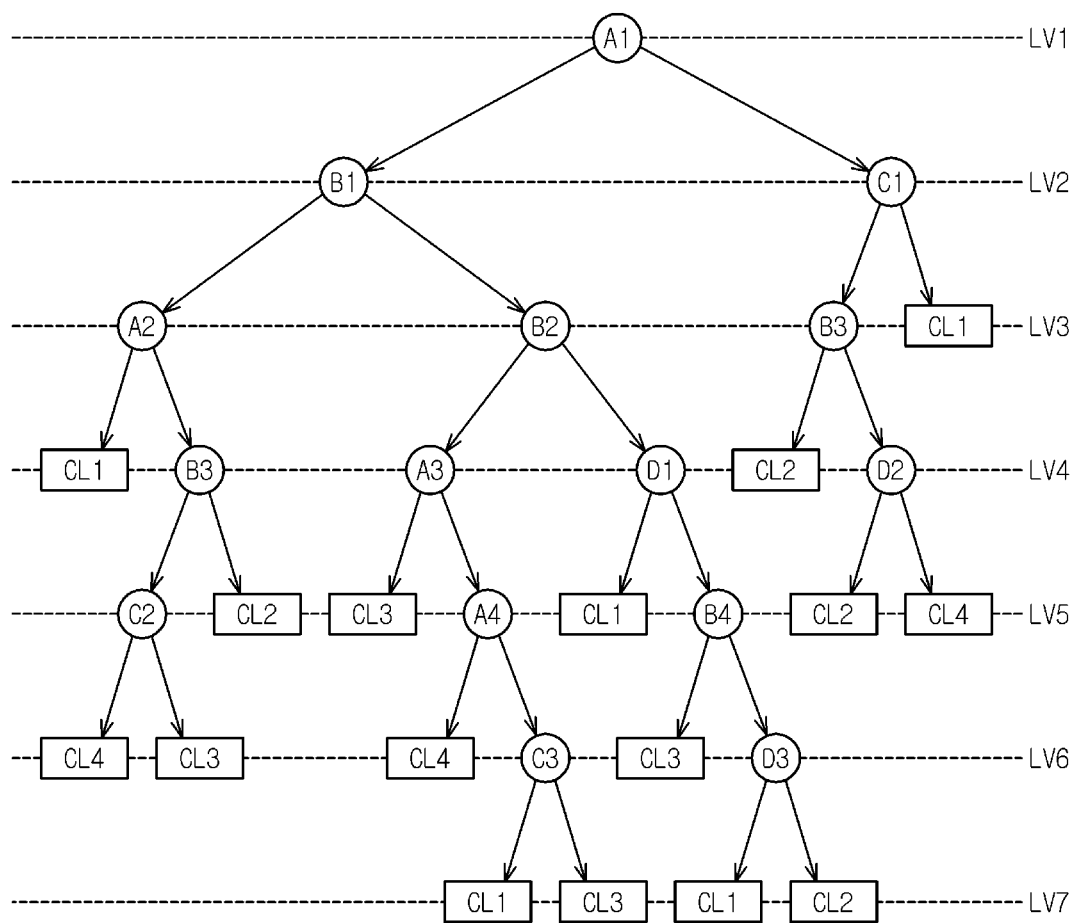
FIG. 4 is an exemplary diagram of a data structure stored in an apparatus.

FIG. 4 is an exemplary diagram of a data structure stored in an apparatus.

As shown in FIG. 4, a data structure including one or more feature points (A1-A4, B1-B4, C1-C3 and D1-D3) is stored in the storage 120 of the apparatus 100.

Each of the feature points (A1-A4, B1-B4, C1-C3, and D1-D3) is a classification criterion of biometric information stored in advance in the data structure.

For example, it may be any criterion, such as whether the size of the pupil is greater than 5 mm, whether the corner of the mouth is raised, whether the voice tone is high, whether the voice is trembling, whether the head is nodding, or whether the heart rate has become faster, according to settings.

When a biometric information group (in) is acquired, the main controller 400 may determine an emotion of the driver based on one or more biometric information values included in the biometric information group (in).

The main controller 400 may classify the biometric information values included in the biometric information group (in) according to the feature points of the pre-stored data structure, and may determine the driver's emotion by combining the classified values of the biometric information values. In this case, the main controller 400 may classify in stages the biometric information values according to the feature points.

For example, in a case where the feature point A1 determined in a first level Lv1 shown in FIG. 4 indicates whether or not the voice tone is high, if it is determined that the driver's voice tone is high, the process may proceed to the feature point B1 of a next lower level Lv2, and if it is determined that the driver's voice tone is not high, the process may proceed to the feature point C1 of the next lower level Lv2. Further, in a case where the feature point B1 indicates whether or not the driver is nodding his/her head, if it is determined that the driver is nodding his/her head at the feature point B1, the process may proceed to the feature point B2 of a next lower level Lv3, and if it is determined that the driver is nodding his/her head at the feature point B1, the process may proceed to the feature point A2 of the next lower level Lv3.

Further, in a case where the feature point A2 indicates whether or not the voice is trembling, if it is determined that the voice is trembling at the feature point A2, it is determined in a next lower level Lv4 that the driver's emotion is "anger CL1", and the process is terminated. However, if it is determined that the voice is not trembling at the feature point A2, the process may proceed to the feature point B3 of the next lower level Lv4.

In a case where the feature point B3 indicates whether or not the mouth size is greater than 10 cm, if it is determined that the mouth size is less than 10 cm at the feature point B3, the process proceeds to the feature point C2 of a next lower level Lv5, and if it is determined that the mouth size is greater than 10 cm at the feature point B3, it is determined in the next lower level Lv5 that the driver's emotion is "tiredness CL2", and the process is terminated.

Further, in a case where the feature point C2 indicates whether or not the heart rate is greater than 100 per minute, if the heart rate is less than 100 per minute at the feature point C2, the main controller 400 may determine in the next lower level Lv6 that the driver's emotion is "serenity CL3", and if the heart rate is greater than 100 per minute at the feature point C2, the main controller 400 may determine in the next lower level Lv6 that the driver's emotion is "tension CL4".

A detailed description of the remaining feature points (A3-A4, B2-B4, C1, C3, and D1-D3) and examples of emotions will be omitted.

The feature points (A1-A4, B1-B4, C1-C3, and D1-D3) may be grouped under criteria for classifying different types of biometric information. For example, as shown in FIG. 4, the group of the feature points A1 to A4 including the same alphabet A may be a group of feature points for the driver's "voice data", the group of the feature points B1 to B4 including the same alphabet B may be a group of feature points for the driver's "image data", the group of the feature points C1 to C3 including the same alphabet C may be a group of feature points for the driver's "heartbeat information", and the group of the feature points D1 to D3 including the same alphabet D may be a group of feature points for the driver's "body temperature information", but the present disclosure is not limited thereto.

A data structure including four emotion values (CL1-CL4) is shown in FIG. 4 and described as an example, but the number of emotion values is not limited thereto. Also, the number of feature points is not limited to that shown in FIG. 4.

On the other hand, a route that runs to a resultant emotion value in the data structure is not limited to one. Referring to FIG. 4, routes for determining the emotion of "anger CL1" may include a first route A1→B1→A2→CL1, a second route A1→B1→B2→D1→CL1, a third route A1→B1→B2→A3→A4→C3→CL1, a fourth route A1→B1→B2→D1→B4→D3→CL1, and a fifth route A1→C1→CL1.

Herein, the routes may pass the same or a different number of levels. The first route proceeds up to the fourth level Lv4, the second route proceeds up to the fifth level Lv5, the third route proceeds up to a seventh level Lv7, and the fourth route proceeds up to the third level Lv3.

When a plurality of different biometric information groups (in1, in2, . . . , inn) corresponding to "anger CL1" are input to the biometric sensor 200, if 60% of the input biometric information groups (in1, in2, . . . , inn) are correctly determined as "anger CL1", the data structure may be said to have "60% accuracy" for the emotion of "anger CL1".

When a plurality of different biometric information groups (in1, in2, . . . , inn) corresponding to "tiredness CL2" are input to the biometric sensor 200, if 40% of the input biometric information groups (in1, in2, . . . , inn) are correctly determined as "tiredness CL2", the data structure may be said to have "40% accuracy" for the emotion of "tiredness CL2".

The accuracy of each emotion value may be obtained experimentally or stored in advance in the storage 120 of the apparatus 100.

The controller 110 may determine a representative accuracy of the data structure based on one or more accuracies of one or more emotion values the data structure includes, the representative accuracy value may be stored in the storage 120. For example, the controller 110 may store an average value of the accuracies of one or more emotion values in the storage 120 as the representative accuracy value of the data structure.

The controller 110 may replace the feature point of the data structure to improve the representative accuracy of the data structure stored in the storage 120.

FIG. 5 is a diagram of a contribution list stored in an apparatus according to an exemplary embodiment of the present disclosure.

The storage 120 may also store a contribution list which includes information about feature points and ranks in contribution of the feature points in addition to the data structure.

The contribution list may be pre-stored in a design or repair process, or may be generated by the controller 110.

When the contribution list is generated by the controller 110, the controller 110 may determine the ranks of the feature points by using an Attribute Subset Evaluation method or a Single Attribute Evaluation method. For example, the controller 100 may determine the importance of a feature point by calculating an acquisition cost value between the emotion value and the feature point, and may assign a higher rank to the feature point having high importance. This importance evaluation method may be called a Gain Ratio Attribute Evaluation.

In another example, the controller 110 may determine the importance of a feature point according to a value of the acquisition information between the emotion value and the feature point, and may assign a higher rank to the feature point having the high importance. This importance evaluation method may be called Information Gain Attribute Evaluation. In addition, through various methods such as Chi-square Attribution Evaluation, the controller 110 may determining the rank of one or more feature points, generate the contribution list of the feature points including the information about the rank of each feature point, and store the generated contribution list in the storage 120.

In addition, the controller 110 may group the feature points of the contribution list by rank for quick evaluation later. For example, a preset number of feature points may be grouped together according to the rank, such as grouping the feature points of the first to third ranks into the first group, grouping the feature points of the fourth to sixth ranks into the second group, and grouping the feature points of the seventh to ninth ranks into the third group.

The controller 110 of the apparatus 100 according to an embodiment may evaluate the accuracy of the data structure by comparing the stored data structure with the contribution list.

Figure 6:
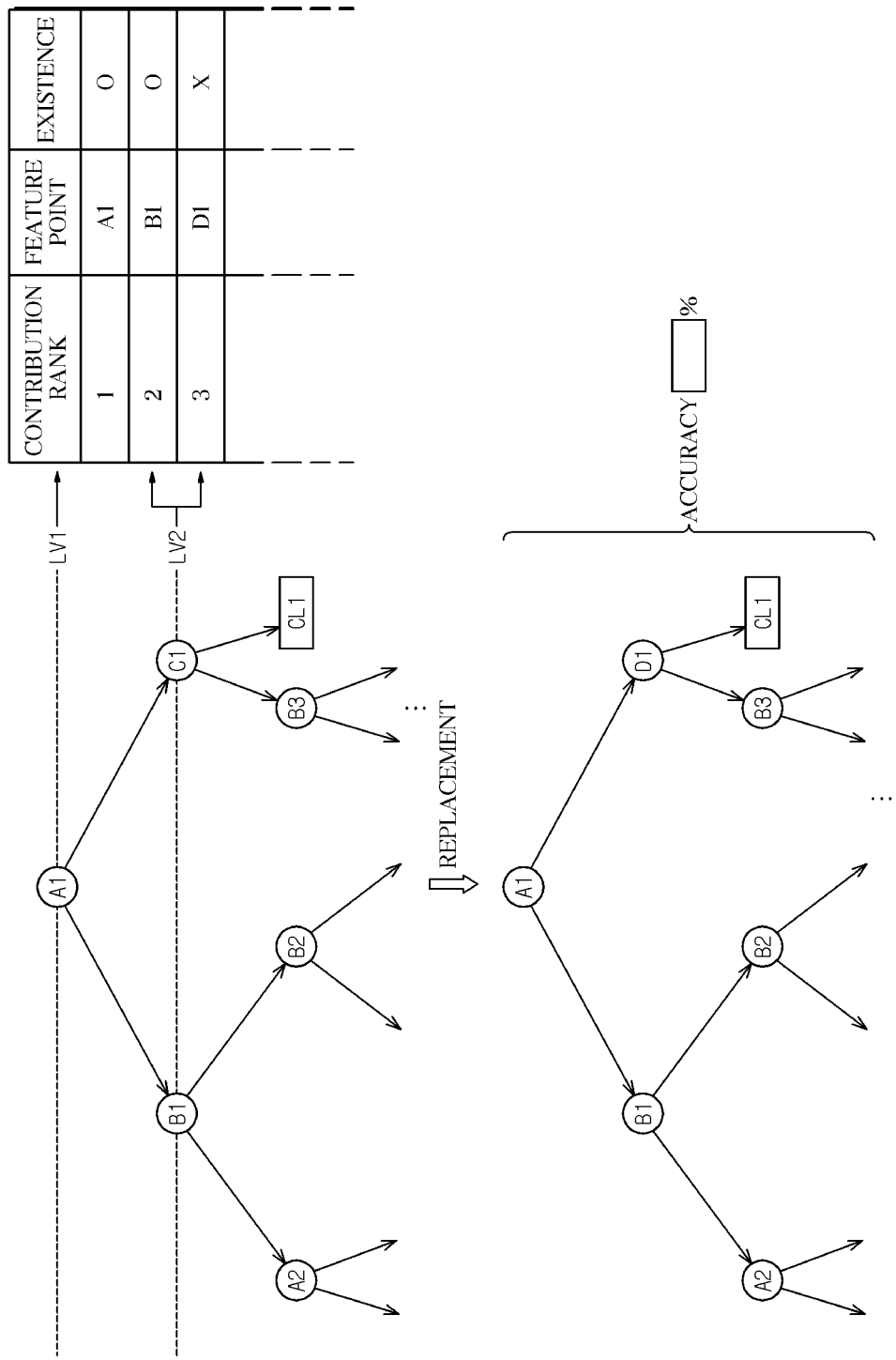
FIGS. 6 and 7 are exemplary diagrams of data structure and contribution list for explaining a process of comparing the data structure and the contribution list.
Figure 7:
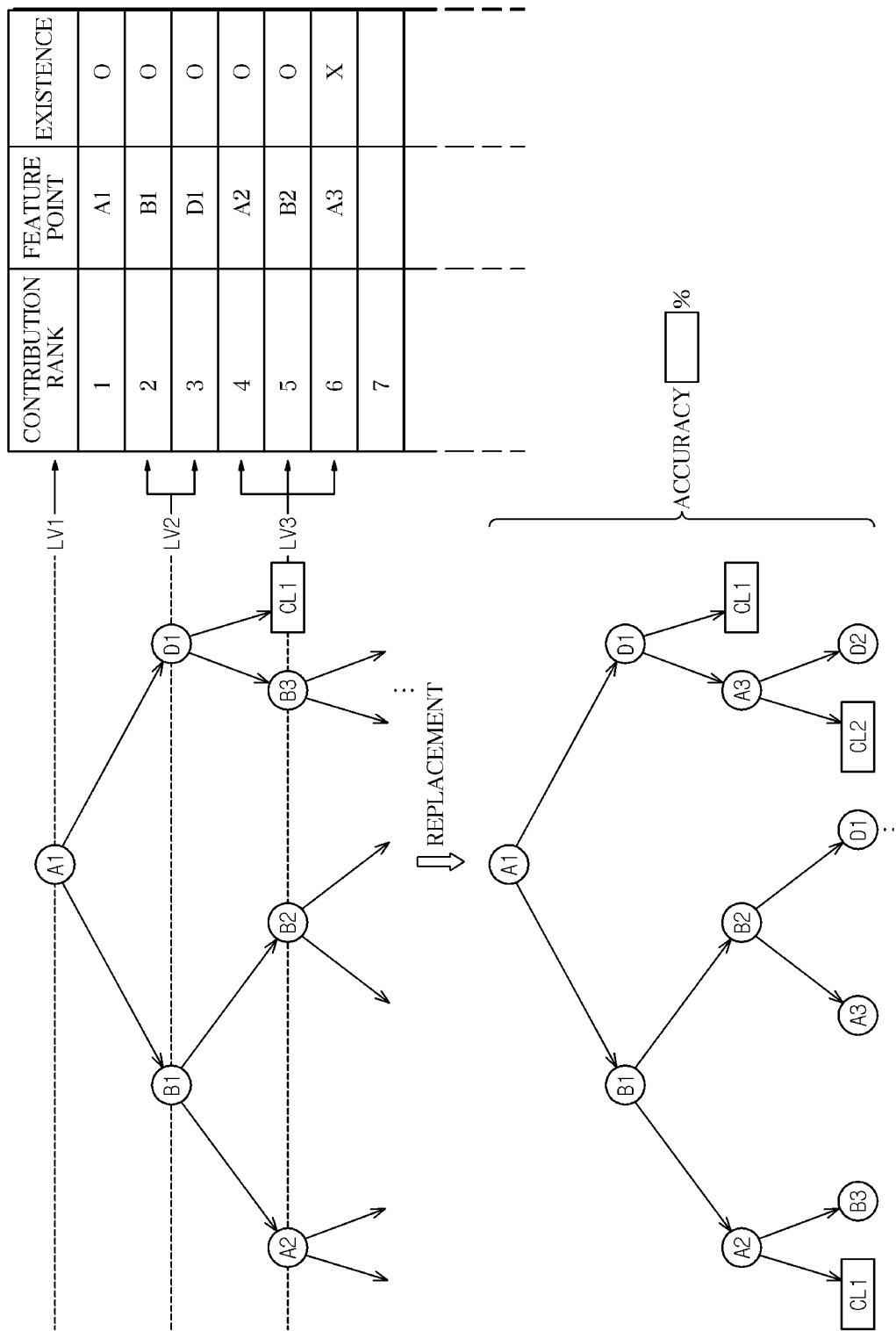

FIGS. 6 and 7 are exemplary diagrams of the data structure and the contribution list for explaining a process of comparing the data structure and the contribution list.

First, the controller 110 may determine whether or not a feature point having the highest rank in the contribution list exists in the first level, which is the highest level in the hierarchy of the data structure.

When there are a plurality of feature points on the first level, the controller 110 may determine whether or not the plurality of feature points in the first level and the plurality of feature points having the highest rank on the contribution list match each other, and may determine whether or not the feature point of the next rank exists on the contribution list in the first level. The number of the plurality of feature points having the highest rank on the contribution list may correspond to the number of the plurality of feature points in the first level.

Referring to FIG. 6, since there is a single feature point A1 in the first level, the controller 110 may determine that the feature point A1 existing in the first level and the feature point A1 having the highest first rank on the contribution list match each other in the data structure, and accordingly, it may be determined that the feature point having the highest rank on the contribution list exists in the first level.

When the feature point in the first level and the feature point having the first rank match each other, the controller 110 may determine whether or not there is a feature point of the next rank on the contribution list in the second level, which is the next level in the hierarchy of the data structure.

When there are a plurality of feature points in the second level, the controller 110 may determine whether or not the plurality of feature points in the second level and the plurality of feature points having the second higher rank to the feature points compared in the previous level on the contribution list match each other, it is possible to determine whether or not the feature point of the next higher rank exists on the contribution list in the second level. Similarly, the number of the plurality of feature points having the second highest rank to the first rank on the contribution list may correspond to the number of the plurality of feature points in the second level.

Referring to FIG. 6, since there are two feature points B1, C1 in the second level, the controller 110 may determine the feature point B1 and the feature point C1 existing in the first level and the feature point B1 and the feature point D1 having the second rank and the third rank, which are the next highest ranks after the feature point A1 compared in the previous first level, match each other in the data structure. Since the feature point B1 but the feature point D1 exists in the second level, the controller 110 may determine that the feature points existing in the second level and the feature points existing on the corresponding rank of the contribution list are mutually inconsistent.

When the feature point in a level and the corresponding feature point on the contribution list do not match each other, the controller 110 may replace the feature point of the level in the data structure with the feature point on the contribution list.

Referring to FIG. 6, the controller 110 may replace the feature point of the second level with the feature point B1 and the feature point D1.

The controller 110 may evaluate the accuracy of the entire data structure when the feature point of a level in the data structure is replaced.

An experimental method may be used for evaluating the accuracy of data structures, without being limited thereto. For example, the accuracy evaluation of a data structure may be performed by various methods including e.g., a cross-validation.

Next, when the accuracy of the data structure is greater than a preset expected value, the controller 110 may store the current data structure with a feature point replaced in the storage 120. When the accuracy of the data structure is less than the expected value, the controller 110 may determine whether or not there is a feature point of the next rank in the third level which is the next higher level in hierarchy to the level that was previously searched. Similarly, the number of the plurality of feature points having a next higher rank than the third highest rank compared last on the contribution list may correspond to the number of the plurality of feature points in the third level.

Referring to FIG. 7, when the accuracy of the data structure is less than the expected value as a result of replacing the feature point of the second level, the controller 110 may compare three feature points A2, B2, and B3 existing in the third level with three feature points A2, B2, and A3 having a fourth rank, a fifth rank, and a sixth rank, which are the next highest ranks to the third rank.

Since the feature points A2 and B2 but the feature point A3 exist on the third level, the controller 110 may determine that the feature points existing in the third level and the feature points existing on the corresponding rank of the contribution list are mutually inconsistent, so that it may be determined that there is no next highest feature point on the contribution list in the third level.

Similarly, when the feature point in a level and the corresponding feature point on the contribution list do not match, the controller 110 may replace the feature point of the level in the data structure with the feature point on the contribution list.

Referring to FIG. 7, the controller 110 may replace the feature point of the third level with the feature points A2 and B2.

The controller 110 may re-evaluate the accuracy of the entire data structure when the feature point of a level in the data structure is replaced.

Then, when the accuracy of the data structure is greater than a preset expected value, the controller 110 may store the current data structure with the feature point replaced in the storage 120. When the accuracy of the data structure is less than the expected value, the controller 110 may determine whether or not there is a feature point of the next rank in the fourth level which is the next level to the level previously searched. Similarly, the number of the plurality of feature points having the next higher rank than the sixth rank compared last on the contribution list may correspond to the number of the plurality of feature points in the third level.

On the other hand, when the accuracy of the data structure is less than the expected value despite the replacement of the feature points described above, the controller 110 may perform a process of comparing the feature points on the data structure and the feature points on the contribution list to the last hierarchy of the data structure.

When the accuracy of the data structure is still less than the expected value even after of the replacement of a feature point as described above, the controller 110 may compare the accuracy of the data structure in which the feature point is replaced with the accuracy of the data structure stored in the storage 120 before the feature point is replaced. When the accuracy of the data structure in which the feature point is replaced is greater than the accuracy of the data structure stored in the storage 120, the controller 110 may store the data structure in which the feature point is replaced in the storage 120. When the accuracy of the data structure in which the feature point is replaced is less than the accuracy of the data structure stored in the storage 120, the controller 110 may maintain the data structure stored in the storage 120.

Thus, the apparatus 100 may evaluate the contribution of a feature point of the data structure in each level, and update itself to have a highly accurate data structure by evaluating the accuracy of the data structure after replacement of a feature point. The main controller 400 of the vehicle 10 may accurately perform determination of the driver's emotion using the updated data structure.

On the other hand, at least one component may be added or omitted depending on the performance of the vehicle 10 and the apparatus 100 shown in FIG. 2. It will be readily understood by those skilled in the art that the mutual position of the components may be changed corresponding to the performance or structure of the system.

Some of the components shown in FIG. 2 may be software and/or hardware components such as Field Programmable Gate Arrays (FPGAs) and Application Specific Integrated Circuits (ASICs).

Hereinafter, a control method of the vehicle including the apparatus 100 according to an embodiment will be described with reference to FIG. 8.

Figure 8:
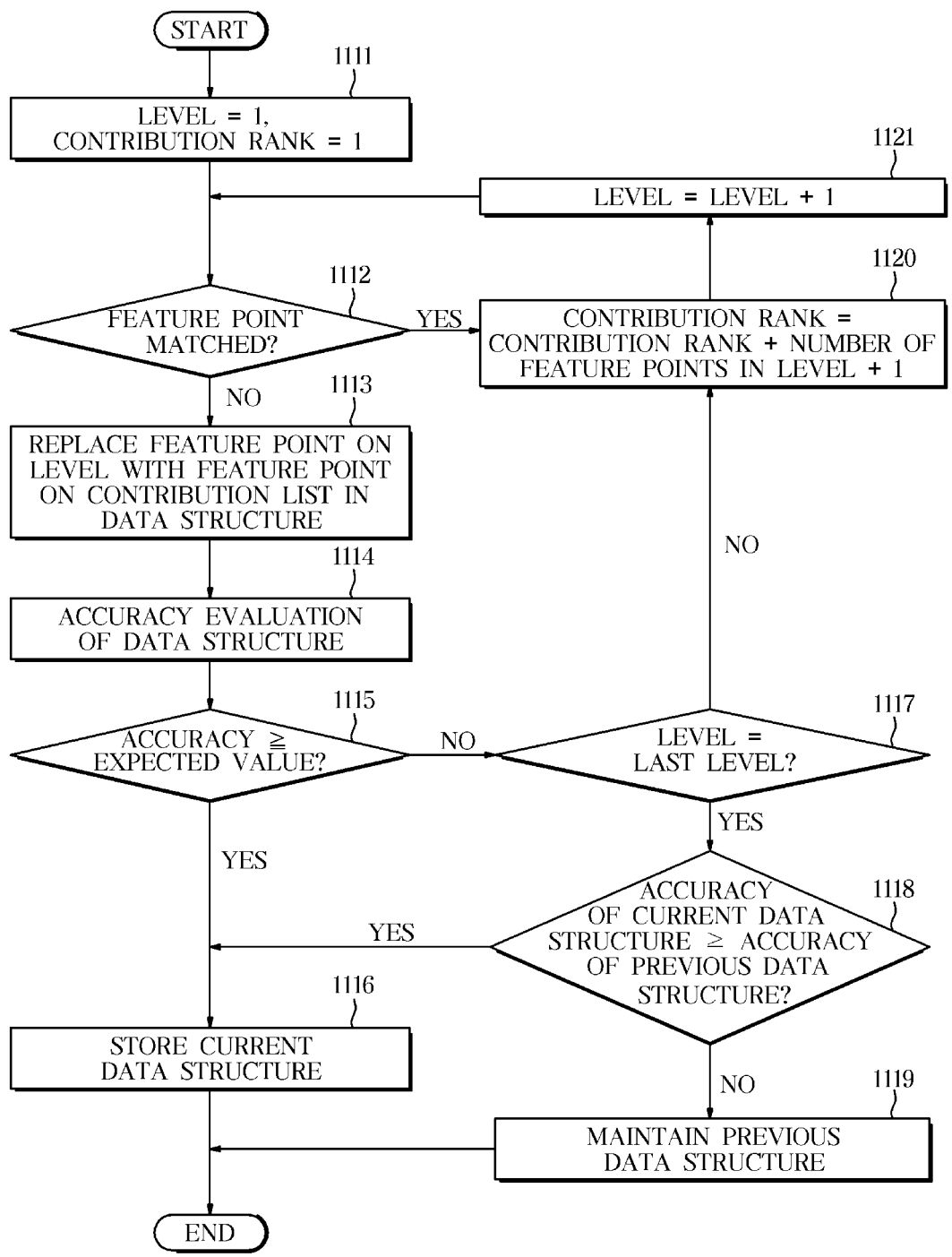
FIG. 8 is a flowchart illustrating a method of controlling a vehicle including the apparatus according to an exemplary embodiment.

FIG. 8 is a flowchart illustrating a method of controlling the vehicle including the apparatus according to an exemplary embodiment.

First, the vehicle 10 having the apparatus for determining driver's emotion according to an exemplary embodiment may determine a feature point of the first level, which is the highest level in hierarchy of the pre-stored data structure, and a feature point of the first rank, which is the highest rank on the pre-stored contribution list (1111), and compare the feature points with each other (1112).

The vehicle 10 then may determine whether a feature point of the first rank on the contribution list exists in the first level on the data structure (1112), and when the feature point of the first rank in the first level of the data structure ("YES" in 1112) exists, the vehicle 10 may compare the feature point of the next level on the data structure with the feature point of the next rank on the contribution list (1120, 1121, 1112).

On the other hand, when there are a plurality of feature points in the first level, the vehicle may extract feature points on the contribution list from the higher rank as many as the number of feature points included in the first level, and compare the feature points included in the first level with feature points extracted from the contribution list.

When the feature points of the first level of the data structure and the plurality of feature points extracted from the contribution list match ("YES" in 1112), the vehicle may compare feature points existing in the next rank (1120; (contribution rank)=(current contribution rank)+(the number of feature points in the first level)+1) of the feature points extracted from the contribution list with feature points of the second level (1120, 1121, 1112). In this case, the vehicle may extract the feature points on the contribution list from the next highest rank as many as the number of feature points included in the second level, and compare the feature points included in the second level with the feature points extracted from the contribution list.

However, when the feature point of the first rank in the first level does not exist, the vehicle may replace the feature point of the level currently searched in the data structure with the feature point extracted from the contribution list (1113).

Then, the vehicle may evaluate the accuracy of the data structure including the replaced feature point (1114), and determine whether the accuracy is equal to or greater than the preset expected value (1115).

When the evaluated accuracy is greater than or equal to the expected value, the vehicle may store the data structure including the replaced feature point (1116). When the evaluated accuracy is less than the expected value, the vehicle may search the next level and compare the feature points existing on the next level with the feature points existing on the next rank of the contribution list (1120, 1121, 1112). When the feature points do not match, the vehicle may replace the feature point as described above, and re-evaluate the accuracy of the replaced data structure to store the data structure with the accuracy above the expected value.

On the other hand, when the vehicle replaces the feature point of the last level in the data structure (1113, 1114) but the accuracy is still below the expected value ("No" in 1115, "YES" in 1117), the vehicle may compare the accuracy of the data structure in which the feature point is replaced with the accuracy of the previously stored data structure (1118), and store the data structure with higher accuracy (1116, 1119).

As is apparent from the above description, using the data structure in which the evaluation is completed by the apparatus according to an aspect of the present disclosure, the vehicle including the same, and the control method of the vehicle, the driver's emotion may be accurately determined based on the biometric information of the driver.

The embodiments of the present disclosure may be implemented in the form of recording media for storing instructions to be carried out by a computer. The instructions may be stored in the form of program codes, and when executed by a processor, may generate program modules to perform an operation in the embodiments of the present disclosure. The recording media may correspond to computer-readable recording media.

The computer-readable recording medium includes any type of recording medium having data stored thereon that may be thereafter read by a computer. For example, it may be a ROM, a RAM, a magnetic tape, a magnetic disk, a flash memory, an optical data storage device, etc.

The exemplary embodiments of the present disclosure have thus far been described with reference to accompanying drawings. It will be obvious to people of ordinary skill in the art that the present disclosure may be practiced in other forms than the exemplary embodiments as described above without changing the technical idea or essential features of the present disclosure. The above exemplary embodiments are only by way of example, and should not be interpreted in a limited sense.

What is claimed is:

1. An apparatus comprising:
    a storage configured to store a data structure including first one or more feature points hierarchically listed and to store a contribution list including information about a contribution rank of each of second one or more feature points; and
    a controller configured to compare the first one or more feature points included in the data structure with the second one or more feature points of the contribution list,
    wherein the controller is further configured to determine whether to update the data structure based on a comparison result.

2. The apparatus according to claim 1, wherein the controller is further configured to replace a feature point in a first hierarchical level among the first one or more feature points with one among the second one or more feature points when the feature point in the first hierarchical level among the first one or more feature points and the feature point among the second one or more feature points match.

3. The apparatus according to claim 1, wherein the controller compares a feature point in a second hierarchical level among the first one or more feature points with one among the second one or more feature points when the feature point in the first hierarchical level among the first one or more feature points and the feature point among the second one or more feature points do not match.

4. The apparatus according to claim 1, wherein the controller compares a feature point in a first hierarchical level among the first one or more feature points with one among the second one or more feature points having a rank corresponding to the first hierarchical level.

5. The apparatus according to claim 4, wherein the controller compares a feature point included in a second hierarchical level, which is a next higher level from the first hierarchical level, among the first one or more feature points with one among the second one or more feature points having a next higher rank when the feature point in the first hierarchical level among the first one or more feature points and the feature point among the second one or more feature points having the rank corresponding to the level do not match.

6. The apparatus according to claim 1, wherein the controller is further configured to replace a feature point in a first hierarchical level among the first one or more feature points with one among the second one or more feature points when the feature point in the first hierarchical level among the first one or more feature points and the feature point among the second one or more feature points match, and to evaluate accuracy of the data structure in which the feature point is replaced.

7. The apparatus according to claim 6, wherein the controller determines whether to update the data structure based on a result of the accuracy evaluation.

8. The apparatus according to claim 6, wherein the controller is further configured to store the data structure in which the feature point is replaced in the storage when the accuracy is equal to or greater than an expected value.

9. A vehicle comprising:
    a biometric sensor configured to collect biometric information of a driver; an apparatus, which includes a controller and a storage, configured to:
    store a data structure including first one or more feature points hierarchically listed and a contribution list including information about a contribution rank of each of second one or more feature points,
    compare feature points included in an hierarchical level of the data structure with feature points of the contribution list, and
    determine whether to update the data structure based on a comparison result; and
    a main controller, which communicates with the biometric sensor and the apparatus, configured to determine a driver's emotion using the data structure and the biometric information.

10. The vehicle according to claim 9, wherein the apparatus is further configured to replace a feature point in a first hierarchical level among the first one or more feature points with one among the second one or more feature points when the feature point in the first hierarchical level among the first one or more feature points and the feature point among the second one or more feature points match.

11. The vehicle according to claim 9, wherein the controller of the apparatus compares a feature point included in a second hierarchical level among the first one or more feature points with one among the second one or more feature points when the feature point in the first hierarchical level among the first one or more feature points and the feature point among the second one or more feature points do not match.

12. The vehicle according to claim 9, wherein the controller of the apparatus compare a feature point included in a first hierarchical level among the first one or more feature points with one among the second one or more feature points having a rank corresponding to the first hierarchical level.

13. The vehicle according to claim 12, wherein the controller of the apparatus compares a feature point included in a second hierarchical level, which is a next higher level from the first hierarchical level, among the first one or more feature points with one among the second one or more feature points having a next higher rank when the feature point included in the first hierarchical level among the first one or more feature points and the feature point among the second one or more feature points having the rank corresponding to the first hierarchical level do not match.

14. The vehicle according to claim 9, wherein the controller of the apparatus is further configured to replace a feature point in a first hierarchical level among the first one or more feature points with one among the second one or more feature points when the feature point included in the first hierarchical level among the first one or more feature points and the feature point among the second one or more feature points match, and evaluates accuracy of the data structure in which the feature point is replaced.

15. The vehicle according to claim 14, wherein the controller of the apparatus determines whether to update the data structure based on a result of the accuracy evaluation.

16. The vehicle according to claim 14, wherein the storage of the apparatus is configured to store the data structure in which the feature point is replaced in the storage when the accuracy is equal to or greater than an expected value.

17. The vehicle according to claim 9, wherein the biometric sensor comprises a camera configured to recognize a driver's face or a hand gesture.

18. The vehicle according to claim 9, wherein the biometric sensor comprises a microphone configured to recognize a driver's voice.

19. The vehicle according to claim 9, further comprising:
a display configured to display a determination result of the driver's emotion.

20. A method for controlling a vehicle, wherein the vehicle includes a storage for storing a data structure including first one or more feature points hierarchically listed and a contribution list including information about a contribution rank of each of second one or more feature points, the method comprising:
comparing, by a controller, a feature point included in a first hierarchical level among the first one or more feature points with one of the second one or more feature points;
determining, by the controller, whether to update the data structure based on a comparison result; and determining, by the controller, a driver's emotion using the data structure and biometric information of the driver.

* * * * *